(12) United States Patent
Stewart

(10) Patent No.: US 8,809,744 B2
(45) Date of Patent: Aug. 19, 2014

(54) WAX REMOVERS FOR SCENT WARMERS AND RELATED METHODS

(75) Inventor: Julie Stewart, Kuna, ID (US)

(73) Assignee: Scentsy, Inc., Meridian, ID (US)

( * ) Notice: Subject to any disclaimer, the term of this patent is extended or adjusted under 35 U.S.C. 154(b) by 35 days.

(21) Appl. No.: 13/092,411

(22) Filed: Apr. 22, 2011

(65) Prior Publication Data
US 2012/0138594 A1 Jun. 7, 2012

Related U.S. Application Data

(63) Continuation-in-part of application No. 29/380,220, filed on Dec. 1, 2010, now Pat. No. Des. 642,705.

(51) Int. Cl.
*F27D 11/00* (2006.01)
*B23P 19/00* (2006.01)

(52) U.S. Cl.
USPC .......... 219/429; 219/386; 392/403; 29/426.5; 222/146.5

(58) Field of Classification Search
USPC ......... 219/386, 428, 429, 438, 422, 424, 432; 392/403, 390; 29/426.5, 270; 222/146.5
See application file for complete search history.

(56) References Cited

U.S. PATENT DOCUMENTS

| | | | |
|---|---|---|---|
| 2,246,346 A | 6/1941 | Wells | |
| 3,475,246 A | 10/1969 | Stafford | |
| 5,654,016 A * | 8/1997 | Shell | 425/87 |
| D642,705 S | 8/2011 | Stewart | |
| 2004/0091184 A1 | 5/2004 | Miller | |
| 2009/0000972 A1 | 1/2009 | Bartusiak | |
| 2009/0004422 A1 | 1/2009 | Bartusiak | |

* cited by examiner

*Primary Examiner* — Shawntina Fuqua
(74) *Attorney, Agent, or Firm* — TraskBritt, P.C.

(57) ABSTRACT

A wax remover for removing solidified wax within a wax container of a scent-warmer device includes a base having a size and shape configured to fit within a wax container of a scent-warmer device, and at least one tab attached to and extending from the base for removing the base from a wax container of a scented warmer device. Such wax removers are used to remove wax from a wax container of a scent-warmer device. A scent-warmer assembly includes a scent-warmer device that comprises a base housing a heat source, and a wax container configured to be heated by the heat source during operation of the scent-warmer device. The assembly further includes a wax remover disposed within the wax container, and a wax disposed at least partially over the wax remover within the wax container.

15 Claims, 5 Drawing Sheets

US 8,809,744 B2

WAX REMOVERS FOR SCENT WARMERS AND RELATED METHODS

CROSS-REFERENCE TO RELATED APPLICATION

This application is a continuation in-part of U.S. Design patent application No. 29/380,220 filed Dec. 1, 2010 entitled "PULL TAB FOR REMOVING SOLIDIFIED SUBSTANCE," now U.S. Design Pat. No. D642,705, issued Aug. 2, 2011, the disclosure of which is incorporated by reference herein in its entirety.

TECHNICAL FIELD

Embodiments of the present invention relate to wax removers for use in scent warmers, assemblies including such wax removers and scent warmers, and methods of using such wax removers.

BACKGROUND

Candles made from scented wax have been used to generate pleasant aromas. Traditionally, candles include a wick that may be lit by a flame. The burning wick melts the wax near the wick and pulls the liquid wax, along with the scented additives incorporated into the wax, up into the wick by capillary action or absorption. The flame burns the scented wax, and the aromas are released into the area surrounding the candle. The flame of the traditional candle also produces light, which is often regarded as desirable for creating a pleasing ambience or for providing energy efficient light. While light and an aroma are produced by such traditional candles, use of such candles is accompanied by the risks and hazards of burns, fires, and smoke.

Recently, scent warmers have been used, as an alternative to candles, to heat scented wax or scented oil and vaporize scent additives therein. Scent warmers are often referred to as flameless candles or wickless candles. Some scent warmers release the aroma from the scented wax or oil without the use of a flame. For example, scent warmers may include a base that houses a heat source such as an incandescent light bulb or a resistive heating element. The heat source is positioned inside the base under a plate holding the scented wax or oil. The heat source heats the bottom of the plate, and the plate, in turn, heats the wax or oil and vaporizes the scent additives therein. The dissipation of the scented vapors provides the pleasant aromas. Such scent warmers are generally safer than traditional candles due to the absence of a flame.

BRIEF SUMMARY

In some embodiments, the present disclosure includes a wax remover for removing re-solidified wax within a wax container of a scented warmer device. The wax remover comprises a base portion having a size and shape configured to fit within a wax container of a scent-warmer device, and at least one elongated tab attached to and extending from the base portion for removing the base from a wax container of a scent-warmer device.

In additional embodiments, the present disclosure includes a scent-warmer assembly that comprises a scent-warmer device, a wax remover, and wax. The scent-warmer device includes a base housing, a heat source, and a wax container configured to be heated by the heat source during operation of the scent-warmer device. The wax remover is disposed within the wax container, and the wax is disposed at least partially over the wax remover within the wax container.

In yet further embodiments, the present invention includes methods of removing a wax from a scent-warmer device. In accordance with such methods, a wax remover is disposed within a wax container of a scent-warmer device, and a wax is placed over the wax remover within the wax container. The wax is melted in the wax container, after which the wax is cooled and re-solidified in the wax container. The wax remover is then removed from the wax container, and the solidified wax is removed from the wax container together with the wax remover.

BRIEF DESCRIPTION OF THE SEVERAL VIEWS OF THE DRAWINGS

While the specification concludes with claims particularly pointing out and distinctly claiming what are regarded as embodiments of the present invention, various features and advantages of embodiments of the disclosure may be more readily ascertained from the following description of example embodiments of the disclosure when read in conjunction with the accompanying drawings, in which:

DETAILED DESCRIPTION

When using a scent warmer that melts wax to release scented additives therein for providing a pleasant aroma, once the scented additives in the wax have been depleted, the wax will need to be removed from the scent warmer and replaced with fresh scented wax if it is desired to replenish the strength of the aroma of the wax. It can be relatively difficult to remove a scented wax from the plate holding the scented wax after the scented wax has melted. Applicant has developed an improved device and method for use in removing scented wax from a scent warmer.

Embodiments of the present invention include a wax remover for removing wax from a wax container of a scent warmer. As used herein, the term "scent warmer" means and includes any device used to melt at least one scented solid substance, such as scented wax, in at least one wax container to generate an aroma. Scent warmers include devices that heat the scented solid substance with a flame, as well as devices that heat the scented solid substance without using a flame using, for example, an incandescent light bulb or a resistive heating element.

Figure 1:
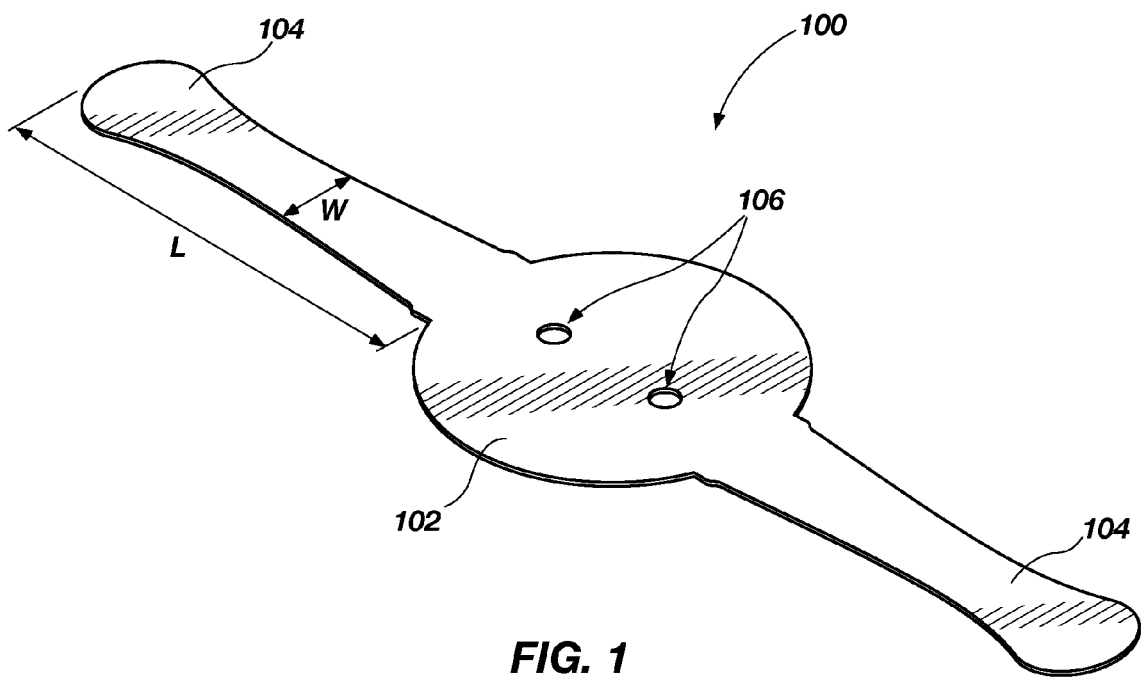
FIG. 1 illustrates an embodiment of a wax remover that includes a base portion and tabs extending from the base portion.

Referring now to the drawings, FIG. 1 is a perspective view of a wax remover 100. The wax remover 100 includes a base portion 102 and at least one tab 104 attached to and extending from the base portion 102. In some embodiments, the at least one tab 104 and the base portion 102 may comprise integral portions of a single, unitary structure. In the embodiment shown in FIG. 1, the wax remover 100 includes two at least substantially identical tabs 104, which are integrally formed with and attached to, and extend from, the base portion 102 on diametrically opposing sides of the base portion 102.

Figure 3:
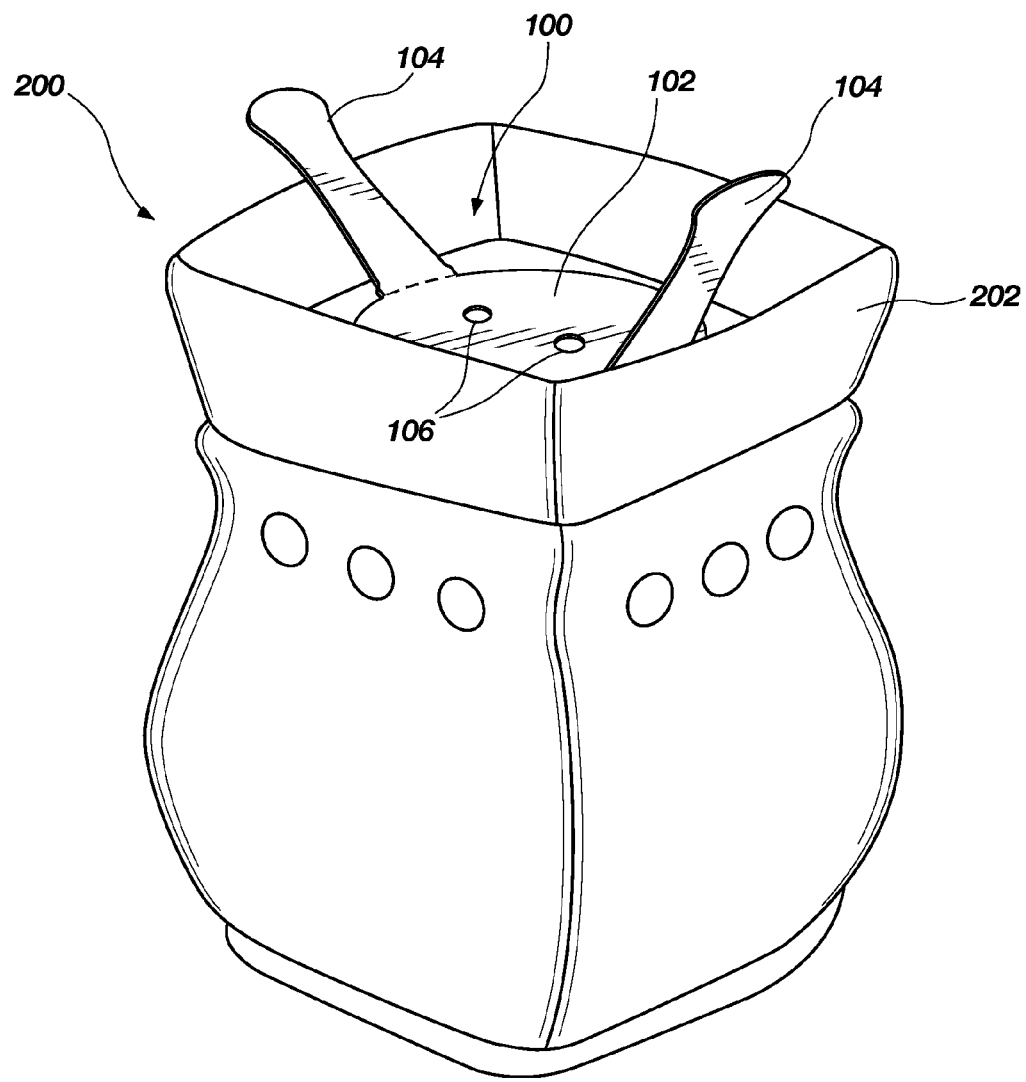
FIG. 3 illustrates an embodiment of an assembly that includes the wax remover of FIG. 1 disposed in a wax container of a scent warmer.

In some embodiments, the base portion 102 may comprise a relatively thin, planar structure having a circular shape, as shown in FIG. 1. In additional embodiments, the base portion 102 may have a shape other than a circle, such as, for example, a square, a triangle, or any polygonal shape. In some embodiments, the base portion 102 may have a size and shape that is configured to conform to the geometry of a surface of a wax container 202 of a scent-warmer device 200 (FIG. 3). In further embodiments, the base portion 102 may have a three-dimensional (3D) structure, such that the base portion 102 may fit within and at least substantially cover an entire area of one or more surfaces of a wax container 202 of a scent-warmer device 200 (FIG. 3). In such embodiments, the base portion 102 of the wax remover 100 may form a complete barrier between the wax container 202 and a wax 300 (FIG. 4) to be heated therein.

The at least one tab 104 of the wax remover 100 may have a size and shape that enables the tab 104 to be easily gripped by a human hand. For example, the at least one tab 104 may have a length L that is at least about one inch (1"), and may have a width W that is at least about one-half inch (½"). Further, the tab 104 may comprise an enlarged portion at an end thereof distal to the base portion 102 to provide a portion of the tab 104 that is relatively easier to grip between a finger and thumb of a human hand. In some embodiments, the at least one tab 104 may be configured to extend outside of the wax container 202 of the scent-warmer device 200 (FIG. 3).

Figure 4:
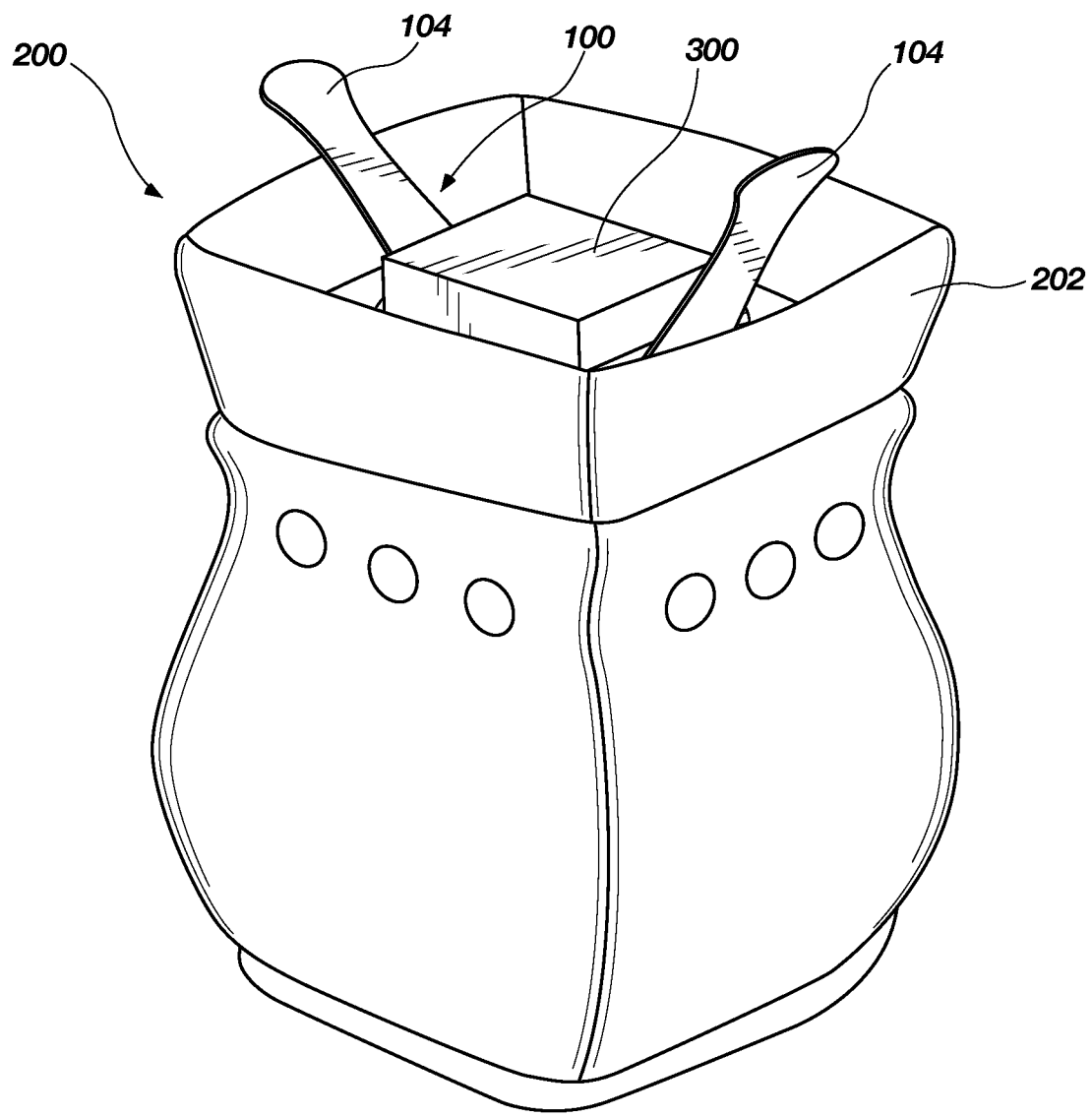
FIG. 4 illustrates a block of un-melted solid scented wax placed over the wax remover in the wax container of the scent warmer shown in FIG. 3.

In some embodiments, the wax remover 100 may comprise a flexible material. The wax remover 100 may also comprise, in some embodiments, a material that is heat resistant. For example, the wax remover 100 may be formed of a material that will resist melting or warping when exposed to temperatures common in the wax container 202 (FIG. 3). For example, the wax remover 100 may be formed of a material resistant to melting or warping at temperatures about the melting temperature of the wax 300 used in the scent-warmer device 200 (FIG. 4). In some embodiments, the wax remover 100 may be formed from and comprise a polymer material, such as a thermoplastic material or a thermoset material. As non-limiting examples, the wax remover 100 may comprise one or more of polyethylene, polystyrene, polyvinyl chloride, and polytetrafluorethylene. In additional embodiments, the scent-wax remover 100 may be formed from and comprise a metal or metal alloy.

In some embodiments, each of the base portion 102 and the at least one tab 104 of the wax remover 100 may be relatively thin. For example, each of the base portion 102, the at least one tab 104, and the wax remover 100 may have a thickness of about one-fourth of an inch (¼") or less, or even about one-sixteenth of an inch (1/16") or less. The wax remover 100 may be sufficiently thin that the wax remover 100 will not prevent transfer of heat from the scent-warmer device 200 to the wax 300 (FIG. 4) in any substantial manner.

In some embodiments, the wax remover 100 may include at least one element configured to improve adherence of the wax 300 (FIG. 4) to the wax remover 100 once the wax 300 has melted and at least partially cooled and re-solidified over the wax remover 100. For example, as shown in FIG. 1, the wax remover 100 may include at least one aperture 106 that extends through the base portion 102 from the major surface on one side thereof to the major surface on an opposing side thereof. The embodiment shown in FIG. 1 includes two circular apertures 106 extending through the base portion 102, although in additional embodiments, more or less apertures 106 may be formed through the base portion 102, and the apertures 106 may have any shape. Upon melting of wax 300 over the base portion 102, the molten wax 300 may infiltrate and fill apertures 106. Upon cooling and re-solidification, the portions of the wax 300 within the apertures 106 may serve to bind the wax 300 to the base portion 102. In additional embodiments, other elements configured to improve adherence of the wax 300 (FIG. 4) to the wax remover 100 may be used. For example, in some embodiments, at least one protrusion, such as a bump or a ridge, may be formed on the base portion 102 of the wax remover 100. Alternatively, in some embodiments, a surface 108 of the wax remover 100 may be roughened to help improve adherence of the wax 300 (FIG. 4) to the wax remover 100.

As previously mentioned, in some embodiments, the at least one tab 104 and the base portion 102 of the wax remover 100 may comprise integral portions of a single, unitary structure. In such embodiments, the wax remover 100 may be formed by cutting or stamping the wax remover 100 out from a substantially planar sheet of polymeric or metallic material. In additional embodiments, the wax remover 100 may be formed using other methods, such as an injection molding process.

Figure 2:
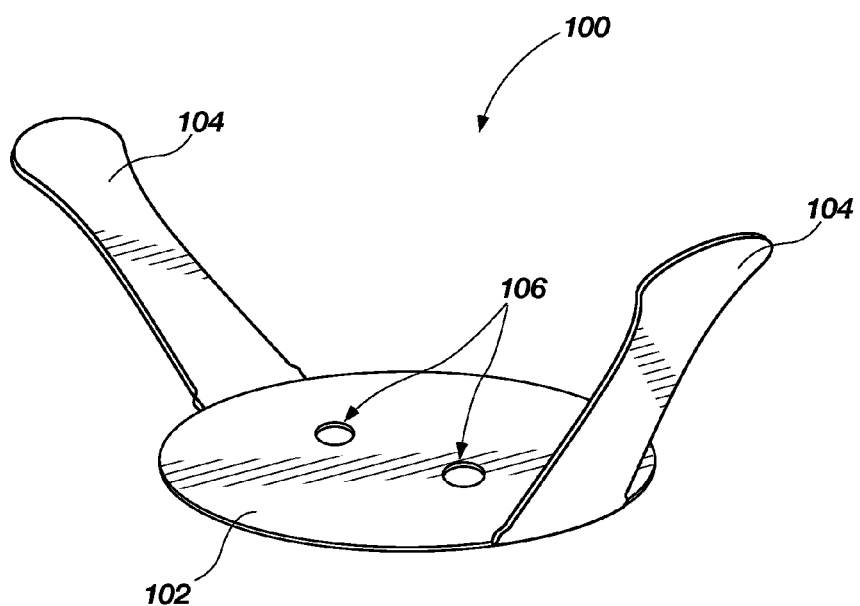
FIG. 2 illustrates the wax remover of FIG. 1 wherein the tabs are bent relative to the base portion.

In some embodiments, the wax remover 100 may be perforated where the at least one tab 104 meets the base portion 102, as shown in FIG. 1, to facilitate bending of the at least one tab 104 relative to the base portion 102. FIG. 2 illustrates the tabs 104 bent relative to the base portion 102. As shown in FIG. 3, in this configuration, the base portion 102 may be positioned within the wax container 202 with the tabs 104 extending outward from, and over, the wax container 202 of the scent-warmer device 200.

Referring to FIG. 4, after placing the wax remover 100 within the wax container 202 of the scent-warmer device 200, a scented substance, such as un-melted solid wax 300, may be positioned over the base portion 102 of the wax remover 100 within the wax container 202. The wax remover 100 is disposed between the wax container 202 of the scent-warmer device 200 and the wax 300.

The scent-warmer device 200 may include any device known in the art for melting the wax 300, and may employ a resistive heating element or an incandescent light bulb to heat and melt the wax 300 (and may not include or employ any flame) within the wax container 202 in some embodiments. In additional embodiments, as previously mentioned, the scent-warmer device 200 may employ any other means for heating and melting the wax 300.

Figure 5:
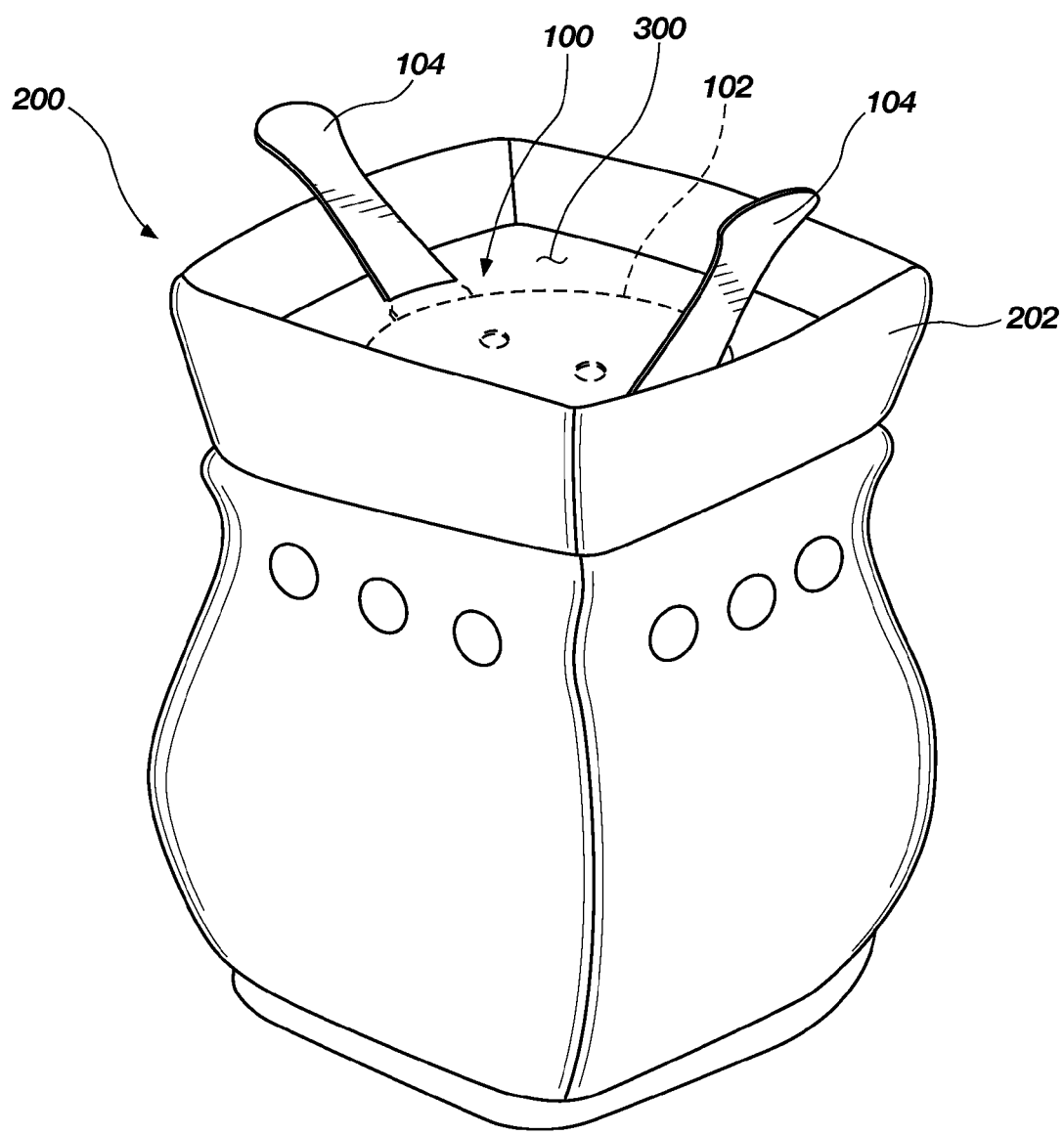
FIG. 5 illustrates the wax in a molten state within the wax container of the scent warmer shown in FIGS. 3 and 4 with the wax remover embedded within the molten wax.
Figure 6:
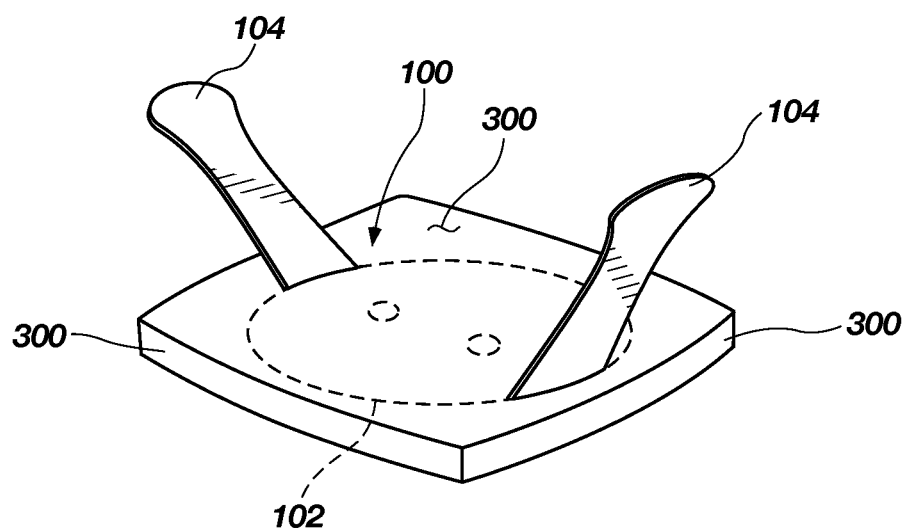
FIG. 6 illustrates the wax remover embedded in the re-solidified wax upon at least partially cooling and re-solidifying the wax, and subsequently removing the wax remover and the wax from the scent warmer by pulling at least one of the tabs of the wax remover.

The scent-warmer device 200 heats the wax container 202, and heat is transferred from the wax container 202 through the wax remover 100 to the wax 300. The heat from the scent-warmer device 200 causes the wax 300 to melt. FIG. 5 illustrates the wax 300 in a molten state within the wax container 202 of the scent-warmer device 200 with the wax remover 100 submerged within the molten wax 300. The wax 300 may include scented additives that produce and release an aroma into the surrounding area.

As previously mentioned, once the scented additives in the wax 300 have been depleted, the wax 300 will need to be removed from the scent-warmer device 200 and replaced with fresh scented wax 300, if it is desired to replenish the strength of the aroma released by the wax 300. To remove the wax 300 from the wax container 202 in accordance with methods of the present disclosure, the heat supplied to the wax 300 may be interrupted, and the wax 300 may be allowed to cool and at least partially re-solidify within the wax container 202 while the wax remover 100 remains submerged within the wax 300. Once the wax 300 has cooled and re-solidified to a sufficiently solid consistency, a person may pull on one or both of the tabs 104 of the wax remover 100 to remove the wax remover 100 from the wax container 202. As the base portion 102 (and portions of the tabs 104) of the wax remover 100 are embedded within the re-solified wax 300, removal of the wax remover 100 from the wax container 202 will also remove the wax 300 from the wax container 202 of the scent-warmer device 200.

As previously described, in additional embodiments, the wax remover 100 may have a three-dimensional cup-shaped structure, and may form a complete barrier between the wax 300 and the wax container 202. In such embodiments, the wax 300 may not need to cool prior to removal of the wax remover 100 and the wax 300 from the wax container 202. Additionally, a scented liquid, such as a scented oil (that is liquid at room temperature), may be used in place of a wax 300 that is solid at room temperature.

As previously discussed, the wax remover 100 may include one or more elements configured to strengthen a bond between the re-solidified wax 300 and the wax remover 100 embedded therein, such as the one or more apertures 106. Such features may help to ensure that the wax 300 is removed from the wax container 202 when the wax remover 100 is removed from the wax container 202. For example, as the wax 300 melts, a portion of the wax 300 may fill the at least one aperture 106. As the wax 300 cools, the portion of the wax 300 filling the at least one aperture 106 in the wax remover 100 may solidify. Accordingly, when the wax remover 100 is removed, the solidified portion of the wax 300 within the wax remover 100 may prevent the wax remover 100 from being removed from the wax container 202 without the wax 300. In other words, the solidified portion of the wax 300 within the at least one aperture 106 may prevent the wax remover 100 from sliding out from between the wax 300 and the wax container 202 without carrying the wax 300 with the wax container 100.

In some embodiments, the wax remover 100 may be further configured such that the wax 300 may be readily removed from the wax remover 100. This allows for the wax remover 100 to be reused, if desired. For example, because the wax remover 100 may be formed of a flexible material, the wax remover 100 may be flexed such that the wax 300 may be removed or "peeled" off the wax remover 100 after the wax remover 100 has been removed from the wax container 202.

By using the wax remover 100 to remove the wax 300 from the wax container 202 of the scent-warmer device 200, the wax 300 may be removed from the wax container 202 while leaving little to no wax residue on the wax container 202. Accordingly, the wax remover 100 provides a means for quickly and cleanly removing the wax 300 from the wax container 202. In addition, the wax remover 100 may allow a wax 300 having a particular scent to be completely removed from the scent-warmer device 200 and replaced with a wax 300 having a different scent. The wax remover 100 may also allow for greater material and design options of the scent-warmer device 200 since the wax remover 100 may provide a barrier between the wax 300 and the scent-warmer device 200.

Embodiments of wax removers as described herein, such as the wax remover 100, may find particular utility with scent-warmer devices 200 in which the wax container 202 is attached to, and not readily separable from the base of the scent-warmer device 200. In such scent-warmer devices 200, it may be relatively more difficult to remove wax 300 from the wax container 202, and, hence, use of wax removers 100, as described herein, may be used to facilitate the removal and replacement of wax 300. For example, some scent-warmer devices 200 are designed and configured such that the base portion of the scent-warmer device 200 plugs directly into an electrical outlet (i.e., socket) on a wall of a building without any electrical cord extending between the base portion and the electrical outlet. In this configuration, the scent-warmer device 200 may be configured to be suspended adjacent the wall by a rigid electrical plug extending laterally from the base portion of the scent-warmer device 200, while the rigid electrical plug is disposed within the electrical outlet. In such embodiments, the wax container 202 is often fixed relative to the base portion of the scent-warmer device 200 and not readily removable therefrom. Embodiments of wax removers, as described herein, such as the wax remover 100, may find particular utility with scent-warmer devices 200.

Additionally, while the embodiments described above are directed toward a wax remover for a scent-warmer device, the wax remover may be used to facilitate removal of other material that is liquefied and re-solidified within a container. For example, a wax remover, as disclosed herein, may be placed between a standard flame candle and a candleholder to catch wax dripping from the candle and to remove the wax drippings from the candleholder.

While the present invention has been described herein with respect to certain illustrated embodiments, those of ordinary skill in the art will recognize and appreciate that it is not so limited. Rather, many additions, deletions and modifications to the illustrated embodiments may be made without departing from the scope of the invention as hereinafter claimed, including legal equivalents thereof. In addition, features from one embodiment may be combined with features of another embodiment while still being encompassed within the scope of the invention as contemplated by the inventors.

What is claimed is:

1. A wax remover for removing re-solidified wax within a wax container of a scent-warmer device, the wax remover comprising:
   a substantially circular, planar base portion having a size and shape configured to fit within a wax container of a scent-warmer device and having at least one feature configured to strengthen a bond between the substantially circular, planar base portion and re-solidified wax, the substantially circular, planar base portion configured to allow molten wax disposed over the base portion to contact adjacent surfaces of a wax container of a scent-warmer device; and
   at least one elongated tab attached to and extending from the base portion for removing the base portion from a wax container of a scent-warmer device.

2. The wax remover of claim 1, wherein at least one of the substantially circular, planar base portion and the at least one elongated tab comprises a material having a melting temperature greater than about one hundred fifty degrees Celsius (150° C.).

3. The wax remover of claim 1, wherein at least one of the substantially circular, planar base portion and the at least one elongated tab comprises a polymer material or a metal material.

4. The wax remover of claim 1, wherein the substantially circular, planar base portion has a thickness of about one-fourth of an inch or less.

5. The wax remover of claim 4, wherein the substantially circular, planar base portion has a thickness of about one-sixteenth of an inch or less.

6. The wax remover of claim 1, wherein the at least one feature comprises at least one of an aperture, a bump, a ridge, and a roughened surface.

7. A scent-warmer assembly, comprising:
   a scent-warmer device comprising:
      a base housing a heat source; and
      a wax container configured to be heated by the heat source during operation of the scent-warmer device;
   a wax remover disposed within the wax container, the wax container separating the wax remover and the base housing; and
   a molten wax disposed at least partially over the wax remover within the wax container, wherein at least a portion of an inner surface of the wax container is in contact with the molten wax within the wax container.

8. The scent-warmer assembly of claim 7, wherein the wax remover comprises a base portion and at least one tab.

9. The scent-warmer assembly of claim 8, wherein the at least one tab extends outside the wax container.

10. The scent-warmer assembly of claim 7, wherein the wax remover comprises at least one aperture extending through the wax remover.

11. The scent-warmer assembly of claim 10, wherein a portion of the wax is disposed within the at least one aperture.

12. A method of removing a wax from a scent-warmer device, comprising:
   disposing a wax remover within a wax container of a scent-warmer device, the wax container separating a scent-warmer device and the wax remover;
   placing a wax over the wax remover within the wax container;
   melting the wax in the wax container and causing at least a portion of an inner surface of the wax container to be in contact with a molten wax in the wax container;
   cooling and solidifying the wax in the wax container; and
   lifting the wax remover from the wax container and removing the solidified wax from the wax container together with the wax remover.

13. The method of claim 12, wherein disposing a wax remover within the wax container of the scent-warmer device comprises disposing a base of the wax remover within the wax container with at least one pull tab attached to the base of the wax remover extending outside of the wax container.

14. The method of claim 13, wherein lifting the wax remover from the wax container comprises pulling on the at least one pull tab of the wax remover.

15. The method of claim 12, wherein melting the wax in the wax container comprises melting a portion of the wax into at least one aperture formed in the wax remover.

* * * * *